United States Patent
Kato et al.

(10) Patent No.: US 10,222,358 B2
(45) Date of Patent: *Mar. 5, 2019

(54) GAS DETECTION SHEET

(71) Applicant: TDK CORPORATION, Tokyo (JP)

(72) Inventors: Tomohiko Kato, Tokyo (JP); Takayuki Maruyama, Tokyo (JP); Rie Ihara, Tokyo (JP)

(73) Assignee: TDK CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/467,272

(22) Filed: Mar. 23, 2017

(65) Prior Publication Data

US 2017/0276657 A1 Sep. 28, 2017

(30) Foreign Application Priority Data

Mar. 28, 2016 (JP) .................. 2016-063488

(51) Int. Cl.

| G01N 33/00 | (2006.01) |
|---|---|
| H01G 11/06 | (2013.01) |
| H01M 10/48 | (2006.01) |
| H01G 11/58 | (2013.01) |
| H01M 10/0525 | (2010.01) |
| H01M 10/42 | (2006.01) |
| H01G 11/20 | (2013.01) |
| H01G 11/54 | (2013.01) |
| H01G 11/82 | (2013.01) |

(52) U.S. Cl.
CPC ..... *G01N 33/0047* (2013.01); *G01N 33/0054* (2013.01); *H01G 11/20* (2013.01); *H01G 11/54* (2013.01); *H01G 11/58* (2013.01); *H01G 11/82* (2013.01); *H01M 10/4228* (2013.01); *H01M 10/488* (2013.01); *H01G 11/06* (2013.01); *H01M 10/0525* (2013.01); *Y02A 50/246* (2018.01); *Y02E 60/13* (2013.01)

(58) Field of Classification Search
CPC .......... G01N 33/0047; G01N 33/0054; H01G 11/06; H01G 11/58; H01M 10/0525; H01M 10/4228; H01M 10/488
USPC ........................................ 422/402
See application file for complete search history.

(56) References Cited

U.S. PATENT DOCUMENTS

| 6,416,905 B1 * | 7/2002 | Bronstert ........... C08G 65/3322 |
| | | 429/212 |
| 6,503,657 B1 * | 1/2003 | Takami ............... H01M 2/0275 |
| | | 429/188 |
| 2004/0043289 A1 * | 3/2004 | Shimamura ......... H01M 2/0212 |
| | | 429/162 |

FOREIGN PATENT DOCUMENTS

| JP | 2005-062026 A | 3/2005 |
| JP | 2009-026569 A | 2/2009 |

OTHER PUBLICATIONS

Niel, V., et al. (2001). Cooperative Spin Crossover Behavior in Cyanide-Bridged Fe(II)-M(II) Bimetallic 3D Hofmann-like Networks (M=Ni, Pd, and Pt). Inorg. Chem. 40: 3838-3839.*

(Continued)

*Primary Examiner* — Jill A Warden
*Assistant Examiner* — Jacqueline Brazin
(74) *Attorney, Agent, or Firm* — Oliff PLC

(57) ABSTRACT

A gas detection sheet wherein a porous coordination polymer represented by formula (1) is supported on a supporter and the air permeability of the gas detection sheet is 0.8 seconds or more and 60 seconds or less.

$$Fe_x(pz)[Ni_{1-y}M_y(CN)_4] \quad (1)$$

(wherein, pz=pyrazine, $0.95 \leq x < 1.05$, M=Pd or Pt, $0 \leq y < 0.15$).

2 Claims, 1 Drawing Sheet

(56) References Cited

OTHER PUBLICATIONS

Tayagaki, T. (2005). Metal Dilution Effects on the Spin-Crossover Properties of the Three-Dimensional Coordination Polymer Fe(pyrazine)[Pt(CN)4). J. Phys. Chem. B. 109(31). 14859-14867. (Year: 2005).*
Niel, Virginie et al., Cooperative Spin Crossover Behavior in Cyanide-Bridged Fe(II)-M(II) Bimetallic 3D Hofmann-like Networks (M=Ni, Pd, and Pt)., Inorg. Chem,vol. 40, pp. 3838-3839, (2001).
Southon, Peter D. et al., "Dynamic Interplay Between Spin-Crossover and Host-Guest Function in a Nanoporous Metal-Organic Framework Material.", JACS Articles, American Chemical Society, pp. 10998-11009, (2009).
Boldog, Ishtvan et al., "Spin-Crossover Nanocrystals with Magnetic, Optical, and Structural Bistability Near Room Temperature.", Angewandte Chemie, vol. 47, pp. 6433-6437, (2008).
Tu Yue et al., "Preparation of WO3 Gas-sensitive Thin Film," Journal of Ceramics, vol. 34, No. 4. Dec. 2013.

\* cited by examiner

GAS DETECTION SHEET

The present invention relates to a gas detection sheet and an electrochemical element with the gas detection sheet.

BACKGROUND

With the decrease in size and increase in functionality of portable electronic devices in recent years, further miniaturization, weight reduction and higher capacity are expected for electrochemical elements.

Electrochemical elements can be made into various forms. A prismatic type, a pillared type and a pouch type or the like can be listed as the representative ones.

Among them, the pouch-type electrochemical element uses a pouch-type case made by sheets such as aluminum laminate film or the like, thus, it is light and can be manufactured into various forms. There is also a strong point in the simple manufacturing process. On the other hand, compared with the pillared type and the prismatic type, the pouch-type has a problem that it is easy to swell due to a flaw or an increase in the inner pressure.

In the electrochemical elements, in a lithium ion secondary battery or a lithium ion capacitor, a mixed solvent of a ring carbonate such as ethylene carbonate and a chain carbonate such as diethyl carbonate is usually used as the electrolyte solvent; in the electric double layer capacitor, acetonitrile, propylene carbonate or the like is used as the electrolyte solvent; and in aluminum electrolytic capacitor, ethylene glycol or the like is used as the electrolyte solvent. When the sealability of the case of the electrochemical element is insufficient or when a pinhole or the like occurs in the case, a part of these solvents will become vapor and be evaporated and there will be problems such as bad smells leaked from the hermetically sealed container or deterioration of the properties.

Various detection methods for leaked gas from the hermetically sealed container are proposed up to the present.

For example, in Patent document 1, a detection method is proposed for detecting the leaked detected gas from the hermetic battery using a gas sensor by manufacturing a hermetic battery in a hermetically sealed container with a detected gas atmosphere such as helium or argon or the like and then removing the detected gas in the hermetically sealed container followed by decompressing.

However, in the detection method of Patent document 1, a hermetically sealed container is required in the manufacturing process, thus, not only the instrument will be in a large scale, but also a detected gas supplying, pressure reducing devices and processes such as sensing for detected gas using a sensor are required. Therefore, there is a problem that the detection cannot be carried out simply. Further, there is a problem that the gas leakage before or after the detecting process cannot be detected.

In addition, in Patent Document 2, a method of detecting a gas in an atmosphere using a gas detection tube which will change color by reacting with a gas component is proposed. However, although it is possible to detect the leakage of the gas from the electrochemical element into the atmosphere, there is a problem that it is impossible to determine the gas leaking position.

Patent Documents

Patent Document 1: JP2009-26569A
Patent Document 2: JP2005-62026A

SUMMARY

The present invention is made in view of the above problems and aims to provide a gas detection sheet which has an excellent visibility and which is possible to determine the gas leaking position with a good sensitivity.

The inventors of the present invention do a lot of research and find that the above aim can be reached by using a gas detection sheet characterized in that a porous coordination polymer represented by formula (1) is supported on a supporter wherein the air permeability is 0.8 seconds or more and 60 seconds or less. And thereby the present invention is completed.

(pz=pyrazine)
($0.95 \leq x < 1.05$, M=Pd or Pt, $0 \leq y < 0.15$)

That is, according to the present invention, the following inventions can be provided.

[1] A gas detection sheet characterized in that a porous coordination polymer represented by formula (1) is supported on a supporter wherein the air permeability is 0.8 seconds or more and 60 seconds or less.

(pz=pyrazine)
($0.95 \leq x < 1.05$, M=Pd or Pt, $0 \leq y < 0.15$)

[2] The gas detection sheet according to [1] characterized in that the one surface of the supporter is covered by a protective layer.

[3] An electrochemical element characterized in comprising the gas detection sheet according to [1] or [2] in the vicinity of the surface wherein the electrochemical element uses an electrolyte containing volatile organic compounds.

According to the present invention, a gas detection sheet which has an excellent visibility and which is possible to determine the gas leaking position with a good sensitivity can be provided.

DETAILED DESCRIPTION OF EMBODIMENTS

Hereinafter, the embodiments for carrying out the present invention will be described in detail with reference to the drawings. However, the present invention is not restricted by the contents disclosed in the following embodiments.

In the gas detection sheet of the present embodiment, a porous coordination polymer represented by formula (1) is supported on a supporter wherein the air permeability is 0.8 seconds or more and 60 seconds or less.

(pz=pyrazine)
($0.95 \leq x < 1.05$, M=Pd or Pt, $0 \leq y < 0.15$)

Figure 1:
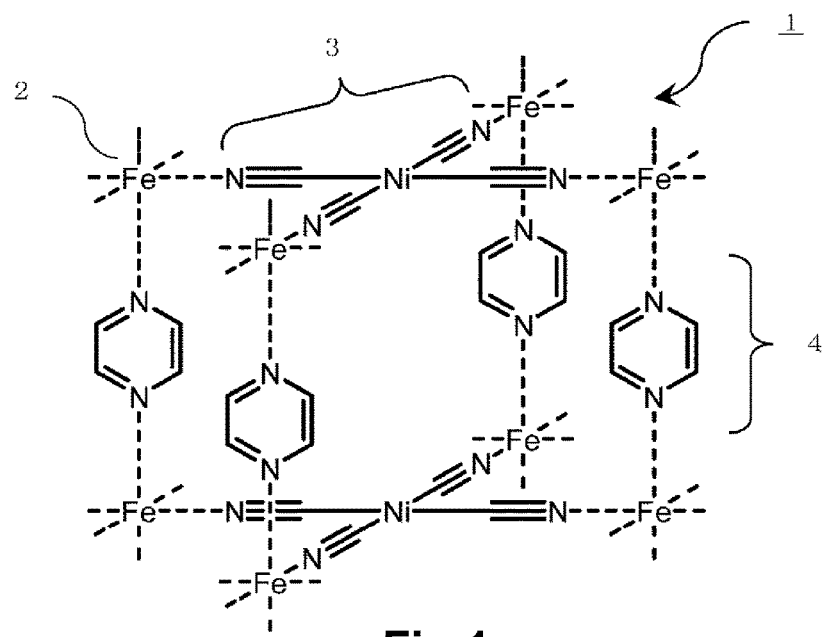
FIG. 1 is a schematic view showing the primary chemical structure of the porous coordination polymer of the present invention.

As shown in FIG. 1, porous coordination polymer 1 has a structure in which tetracyanonickelate ion 3 and pyrazine 4 are in regular coordination by self-assembly on ferrous ion 2 and the jungle gym type skeleton is grown, and the inner space can absorb a variety of molecules or the like. In addition, a part of nickel can be replaced by at least one selected from palladium and platinum.

In porous coordination polymer 1, a phenomenon called as spin crossover is noticed, wherein the electron configuration of ferrous ions varies between two states which are called as high-spin state and low-spin state by external stimulations such as heat, pressure, or the adsorption of molecule. The spin variation can be considered to be in several tens of nano-seconds and has a character of a very high response speed.

The high-spin state refers to the state where the electrons are configured in a way that the spin angular momentum becomes the biggest according to the Hund's rule in the 5 orbits of the d electron of the ferrous ions in the complex. The low-spin state refers to the state where the electrons are configured in a way that the spin angular momentum becomes the smallest. The two states are different in the states of the electron and the crystal lattices, thus, the colors and the magnetisms of the complexes in the two states are different. That is, the gas can be detected with excellent visibility and sensitivity by using the spin crossover phenomenon caused by the adsorption of the molecule to the porous coordination polymer.

The porous coordination polymer in the high-spin state is orange and it will turn to reddish purple of the low-spin state if it is cooled sufficiently by liquid nitrogen or the like. In addition, if it is exposed in the gas of specific organic compounds such as acetonitrile or acrylonitrile or the like, the gas will be adsorbed into the inner of the crystal and turn to be the low-spin state. If the porous coordination polymer of reddish purple in the low-spin state is exposed in the organic compound gas which induces the high-spin state, it will take gas into the inner of the jungle gym type skeleton and turn to be orange of the high-spin state by the spin crossover phenomenon. As the gases of the organic compounds, vapors such as organic combustible gas or volatile organic solvent or the like can be listed as examples. That is, the porous coordination polymer in the low-spin state adsorbs gas(es) such as dimethyl carbonate (hereinafter, referred as DMC), diethyl carbonate (hereinafter, referred as DEC), and ethyl methyl carbonate (hereinafter, referred as EMC) or the like which is/are solvent(s) contained in the electrolyte for lithium ion secondary battery or lithium ion capacitor; or gas(es) such as ethylene and propylene or the like which is/are produced by the decomposition of the solvent(s) mentioned above; or further gas(es) such as propylene carbonate or the like which is solvent contained in the electric double layer capacitor; or further gas(es) such as ethylene glycol or the like which is solvent contained in the electrolyte for aluminum electrolytic capacitor, and turns to be orange in the high-spin state.

Refer to the composition of the porous coordination polymer of present embodiment, it can be confirmed by methods such as ICP (inductively coupled plasma) atomic emission spectroscopy, X-ray fluorescence elemental analysis, carbon/sulfur analysis and oxygen/nitrogen/hydrogen analysis or the like.

The spin state of the porous coordination polymer of the present embodiment can be confirmed by observing the response of the magnetization relative to the magnetic field using superconducting quantum interference device (SQUID) or vibrating sample magnetometer (VSM).

In the manufacture method of the porous coordination polymer of the present embodiment, first, carry out a reaction of the ferrous salt, antioxidant, tetracyanonickelate, tetracyanopalladate and tetracyanoplatinate in a proper solvent to obtain an intermediate. Then disperse the intermediate in a proper solvent and a precipitate can be precipitated by adding pyrazine into the dispersion liquid. The porous coordination polymer can be obtained by filtrating and drying the precipitate.

As the ferrous salt, ferrous sulfate heptahydrate, ammonium iron(II) sulfate hexahydrate or the like can be used. As the antioxidant, L-ascorbic acid or the like can be used. As the tetracyanonickelate, potassium tetracyanonickelate(II) hydrate or the like can be used. As the tetracyanopalladate, potassium tetracyanopalladate(II) hydrate or the like can be used. As the tetracyanoplatinate, potassium tetracyanoplatinate(II) hydrate or the like can be used.

As the solvent, methanol, ethanol, propanol, water and the like, or a mixed solvent thereof and the like can be used.

Figure 2:
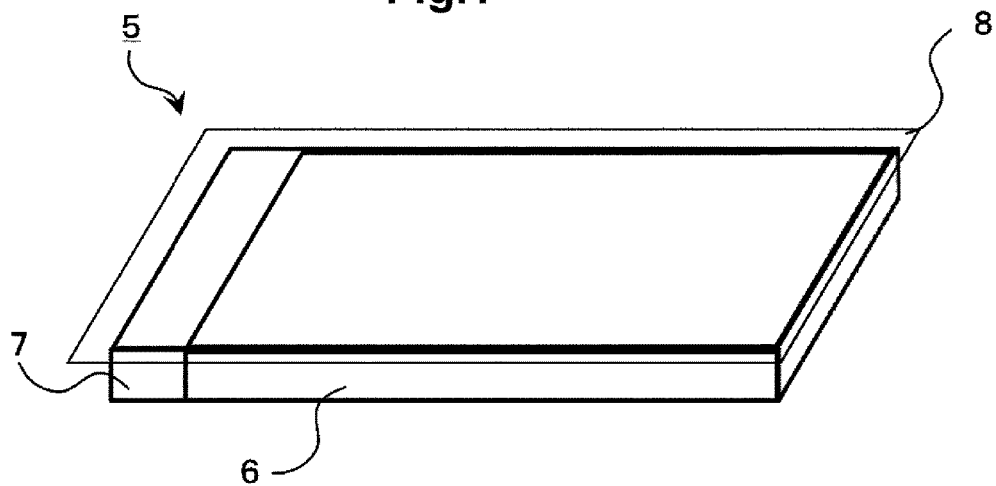
FIG. 2 is a schematic view showing the gas detection sheet of the present invention.

FIG. 2 is a schematic view showing the gas detection sheet of the present embodiment. In FIG. 2, gas detection sheet 5 is composed of porous coordination polymer 6, supporter 7 and protective layer 8.

In gas detection sheet 5 of the present embodiment, porous coordination polymer 6 is supported on supporter 7. When the air permeability is 0.8 seconds or more, the detection gas tends to diffuse inside the supporter, the color tone change of the porous coordination polymer becomes obvious; further, the gas leaking position can be easily identified from the color tone change of the porous coordination polymer caused by the detection gas which has permeated through the supporter. In addition, when the air permeability is 60 seconds or less, even when the amount of the detection gas is small, the color tone change of the porous coordination polymer caused by the detection gas which has permeated through the supporter is obvious, and the gas leaking position can be easily identified. When the air permeability is 0.7 second or less, the pores of the supporter become large and a tendency can be found that the color tone change of the supported porous coordination polymer becomes unobvious. Also, when the air permeability is 65 seconds or more, a tendency can be found that the color change becomes unobvious when the detection gas is small in amount, and it is thought to be due to that it takes time until the detection gas permeates through the supporter, and further the amount of gas adsorbed by the supporter is increased.

The gas detection sheet of the present invention not only can detect the gas from the surface of the detection sheet, but also can detect the gas which permeates through the supporter of the detection sheet with good sensitivity. By using the gas detection sheet of the present embodiment, the gas leaking position can be determined without need of taking the gas detection sheet off from the electrochemical element by evaluating the color tone change of the porous coordination polymer due to the gas which permeates through the supporter of the detection sheet.

As supporter 7, for example, a cellulose-based cardboard such as a filter paper or the like or a rayon-based or polyester-based paper filter, or the like can be used. In addition, the color of the supporter is preferred to be a color which is the complementary color relative to the color after the change caused by the adsorption of the detection gas by the porous coordination polymer, or white, grey or black because these colors can improve the visibility of the color change. Further, the thickness of the supporter is not particularly limited, but it is preferably 50 to 2000 μm from the viewpoint of easy handling during the manufacturing or using of the gas detection sheet.

In the gas detection sheet of the present embodiment, it is preferable that the one surface is covered by protective layer 8. The material of the protective layer is not particularly limited as long as it does not affect the spin state of the porous coordination polymer. For example, a polyethylene terephthalate film, a polyvinylidene chloride film, a polyethylene film or the like, a silicon resin, a polyimide resin, or the like can be listed. In addition, it is preferred that the protective layer has a transmissivity of visible light of 70% or more, and a color tone change of the porous coordination polymer can be confirmed through the protective layer. Further, the protective layer preferably has low moisture permeability and permeability of volatile organic compounds, and thus can suppress color tone change of the porous coordination polymer due to water vapor and volatile organic compounds in the test environment. The protective layer may be adhered to the gas detection sheet with an adhesive, double-sided tape or the like.

The supporting method of the porous coordination polymer onto the supporter is not particularly limited, a filtration method, a spray coating method, a brush coating method and a dip coating method or the like can be listed.

(Measuring of the Supporting Amount of the Gas Detector)

The calculating method of the supporting amount of the porous coordination polymer per area of the gas detector of the present embodiment is as follows. The thin film fundamental parameter method of X-ray fluorescence analysis method is used to measure 10 points in the region where the porous coordination polymer of the detector is supported. The supporting amount of the porous coordination polymer is calculated from the obtained average supporting amount of Fe element. The measuring is performed using an instrument of ZSX 100e made by Rigaku Corporation, with a measuring spot diameter $\phi$ of 3 mm (SUS mask holder with a $\phi$ of 5 mm). The blank measurement value of the supporter is removed in the standard with difference intensity to determine the supporting amount of Fe element per area. The supporting amount of the porous coordination polymer is calculated from the amount ratio of the porous coordination polymer relative to the Fe element which is determined by the composition analysis of the porous coordination polymer.

(Measuring of the Air Permeability)

The air permeability of the gas detection sheet of the present embodiment is obtained by measuring the time cost by 300 ml of air to pass through the gas detection sheet under a certain pressure. The diameter $\phi$ of the measuring portion is 10 mm and the measuring method follows JIS 8117.

The electrochemical element of the present embodiment is characterized in that an electrolyte containing a volatile organic compound is used and the gas detection sheet is provided in the vicinity of the surface.

By providing the gas detection sheet of the present embodiment in the vicinity of the surface of an electrochemical element using an electrolyte containing a volatile organic compound, when the sealability of the case of the electrochemical element is insufficient or when a pinhole or the like occurs in the case, the leaked gas from the electrochemical element can be easily and sensitively detected by evaluating the color tone change of the gas detection sheet.

By using the gas detection sheet of the present embodiment, it is possible to detect the leaked gas from the electrochemical element even during processes other than the inspection process, or during transportation and storage, or the like.

EXAMPLES

Hereinafter, the present invention is further specifically described based on the examples. However the present invention is restricted by the following examples.

Example 1

(Preparation of the Porous Coordination Polymer)

Into an Erlenmeyer flask added with 240 mL of mixed solvent of distilled water and ethanol, 0.24 g of ammonium iron(II) sulfate hexahydrate, 0.1 g of L-ascorbic acid and 0.15 g of potassium tetracyanonickelate (II) monohydrate were added and stirred. The precipitated intermediate particles were collected and 0.1 g of the obtained intermediate particles were dispersed in the ethanol and 0.10 g of pyrazine was added in to it using 30 minutes. The deposited precipitate was filtrated and dried in atmosphere under 120° C. for 3 hours to obtain the orange porous coordination polymer.

(Manufacturing of the Gas Detection Sheet)

The porous coordination polymer of Example 1 was impregnated in acetonitrile under 25° C. for 10 hours. After that, it was suction-filtrated using filter paper No. 5C and dried to form a reddish purple porous coordination polymer on the filter paper No. 5C. For the obtained reddish purple porous coordination polymer, the spin state was confirmed using superconducting quantum interference device (SQUID) and the result was low-spin state. 10 mg of the obtained porous coordination polymer was dispersed in 35 ml of acetonitrile to prepare a dispersion solution and the dispersion solution was placed in a SUS vat, and a roll paper having a thickness of 0.5 mm and an air permeability of 10 seconds was immersed in the dispersion solution. The SUS vat was vibrated and then settled for 5 minutes. Thereafter, the roll paper was slowly taken out from the dispersion solution and dried to complete the gas detection sheet.

(Measurement for the Supporting Amount of the Gas Detection Sheet)

As for the supporting amount of the porous coordination polymer per area of the obtained gas detection sheet, it was measured by the X-ray fluorescence analysis method mentioned above and the result was 0.1 mg/cm$^2$.

(Measuring of the Air Permeability of the Gas Detection Sheet)

As for the air permeability of the obtained gas detection sheet, it was measured by methods mentioned above, and the result was 10 seconds.

(Detection of Diethyl Carbonate Gas)

A small fan and the gas detection sheet were put into a Tedlar bag of 5 L. Nitrogen containing DEC was fed into it to obtain a concentration of 6 ppm. The gas detection sheet was confirmed to turn orange after 63 minutes. On the other hand, in the case where only nitrogen was fed, a color tone change could not be confirmed. Thereby, it could be confirmed that DEC can be detected by evaluating the change of the color tone of the gas detection sheet.

(Detection of Other Gases)

Replacing DEC, ethylene, propylene, toluene, xylene, acetone, ethyl acetate, tetrahydrofuran, methanol, ethanol, n-propanol, isopropanol, ethylene glycol, ammonia, dimethylamine, trimethylamine, triethylamine, acetic acid, formaldehyde, acetaldehyde, diethyl ether, dimethyl carbonate (DMC), ethyl methyl carbonate (EMC) and propylene carbonate was used, the change of the color tone of the gas detection sheet was confirmed in the same way, and the result was that the color changed to be orange.

(Detection of the Leaked Gas of the Lithium Ion Secondary Battery and Determination of the gas Leaking Position)

Two lithium ion secondary batteries were prepared. Among these batteries, a pinhole was punched artificially at a place near the positive electrode terminal of the lithium ion secondary battery using needle to simulate the condition when a pinhole was existed on the case. The batteries were wrapped using the gas detection sheet of Example 1 respectively and then put into the Tedlar bags and sealed to be placed for 63 minutes. The color tone changes of the gas detection sheets were evaluated. As the result, it was confirmed that the color of the vicinity of the positive electrode terminal of the lithium ion secondary battery formed with pinhole changed to be orange. 10 µL of gas in the Tedlar bag was fetched using a gas-tight syringe and the components were analyzed using a gas chromatograph, and as the result, about 6 ppm of DEC was detected. On the other hand, the gas in the Tedlar bags with the lithium ion secondary battery of which the gas detection sheet did not change was fetched and the content was analyzed. As the result, no gas content from electrolyte solution could be detected.

(Detection of the Leaked Gas of the Electric Double Layer Capacitor and Determination of the Gas Leaking Position)

Two electric double layer capacitors containing propylene carbonate in the electrolyte were prepared. Among these capacitors, a pinhole was punched artificially at a place near the positive electrode terminal of the capacitors using needle to simulate the condition when a pinhole was existed on the case. The capacitors were wrapped using the gas detection sheet of Example 1 respectively and then put into the Tedlar bags and sealed to be placed for 66 minutes. It was confirmed that the color of the vicinity of the positive electrode terminal of the electric double layer capacitor formed with pinhole changed to be orange. 10 µL of gas in the Tedlar bag was fetched using a gas-tight syringe and the components were analyzed using a gas chromatograph, and as the result, about 9 ppm of propylene carbonate was detected. On the other hand, the gas in the Tedlar bags with the electric double layer capacitor of which the gas detection sheet did not change color was fetched and the content was analyzed. As the result, no gas content from electrolyte solution could be detected.

Examples 2 to 5 and Comparative Examples 1 and 2

Gas detection sheets were prepared in the same way as in Example 1 except that the concentration of the acetonitrile dispersion solution of the porous coordination polymer was changed to obtain a supporting amount of the porous coordination polymer per area of the gas detection sheet of 0.1 mg/cm$^2$. The air permeability of the gas detection sheet and the time when the color tone change of the gas detection sheet in the detection test of DEC gas was visually observed were shown in Table 1.

TABLE 1

| | Composition of the porous coordination polymer | Air permeability (Seconds) | Visually observed time when the color tone change (minutes) |
|---|---|---|---|
| Example 1 | $Fe_{0.99}(pz)[Ni_{1.0}(CN)_4]$ | 10 | 63 |
| Example 2 | $Fe_{0.99}(pz)[Ni_{1.0}(CN)_4]$ | 0.8 | 63 |
| Example 3 | $Fe_{0.99}(pz)[Ni_{1.0}(CN)_4]$ | 30 | 64 |
| Example 4 | $Fe_{0.99}(pz)[Ni_{1.0}(CN)_4]$ | 50 | 66 |
| Example 5 | $Fe_{0.99}(pz)[Ni_{1.0}(CN)_4]$ | 60 | 68 |
| Comparative example 1 | $Fe_{0.99}(pz)[Ni_{1.0}(CN)_4]$ | 0.7 | Unobviousness, could not be visually observed |
| Comparative example 2 | $Fe_{0.99}(pz)[Ni_{1.0}(CN)_4]$ | 65 | Unobviousness, could not be visually observed |

(pz = pyrazine)

(Detection of Diethyl Carbonate Gas)

For the gas detection sheet of Examples 2 to 5, color tone change caused by DEC gas was evaluated in the same way as Example 1, and as the result, it was confirmed that the gas detection sheet turned to be orange. For the gas detection sheet of Comparative examples 1 and 2, color tone change caused by DEC gas was evaluated in the same way as Example 1, and as the result, the color tone changes after 80 minutes were unobviousness and thus could not be visually observed.

(Detection of the Leaked Gas of the Lithium Ion Secondary Battery and Determination of the Gas Leaking Position)

For the gas detection sheets of Examples 2 to 5, detection of the leaked gas of the lithium ion secondary battery and determination of the gas leaking position were evaluated in the same way as Example 1, and the color tone change of the gas detection sheet was evaluated in the same way as Example 1. As the result, it was confirmed that the color of the vicinity of the positive electrode terminal in the lithium ion secondary battery formed with pinhole changed to be orange. For the gas detection sheets of Comparative Examples 1 and 2, detection of the leaked gas of the lithium ion secondary battery and determination of the gas leaking position were evaluated in the same way as Example 1, and the color tone change of the gas detection sheet was evaluated in the same way as Example 1. As the result, it was confirmed that the color tone changes after 80 minutes were unobviousness and thus could not be visually observed.

Examples 6 to 15, Comparative Examples 3 to 5

Porous coordination polymers were prepared in the same way as in Example 1 except that ammonium iron(II) sulfate hexahydrate, potassium tetracyanonickelate (II) monohydrate, potassium tetracyanopalladate(II) hydrate and potassium tetracyanoplatinate(II) hydrate were weighed to obtain the compositions as shown in Table 2 and gas detection sheets were prepared in the same way as in Example 1 except that the concentration of the acetonitrile dispersion solution of the porous coordination polymer was changed to obtain a supporting amount of the porous coordination polymer per area of the gas detection sheet of 0.1 mg/cm$^2$. The air permeability of the gas detection sheet and the time when the color tone change of the gas detection sheet in the detection test of DEC gas was visually observed calculated by the same way as Example 1 were shown in Table 2.

TABLE 2

|  | Composition of the porous coordination polymer | Air permeability (Seconds) | Visually observed time when the color tone change (minutes) |
|---|---|---|---|
| Example 6 | $Fe_{0.98}(pz)[Ni_{0.98}Pd_{0.02}(CN)_4]$ | 10 | 64 |
| Example 7 | $Fe_{0.95}(pz)[Ni_{0.98}Pd_{0.02}(CN)_4]$ | 10 | 65 |
| Example 8 | $Fe_{1.05}(pz)[Ni_{0.98}Pd_{0.02}(CN)_4]$ | 10 | 65 |
| Example 9 | $Fe_{0.98}(pz)[Ni_{0.98}Pd_{0.02}(CN)_4]$ | 10 | 64 |
| Example 10 | $Fe_{0.98}(pz)[Ni_{0.98}Pt_{0.02}(CN)_4]$ | 10 | 64 |
| Example 11 | $Fe_{1.02}(pz)[Ni_{0.98}Pt_{0.02}(CN)_4]$ | 11 | 66 |
| Example 12 | $Fe_{0.98}(pz)[Ni_{0.94}Pt_{0.06}(CN)_4]$ | 10 | 64 |
| Example 13 | $Fe_{0.98}(pz)[Ni_{0.98}Pd_{0.01}Pt_{0.01}(CN)_4]$ | 10 | 64 |
| Example 14 | $Fe_{0.98}(pz)[Ni_{0.86}Pt_{0.09}(CN)_4]$ | 11 | 66 |
| Example 15 | $Fe_{0.98}(pz)[Ni_{0.86}Pt_{0.14}(CN)_4]$ | 11 | 67 |
| Comparative example 3 | $Fe_{0.94}(pz)[Ni_{0.98}Pd_{0.02}(CN)_4]$ | 13 | Unobviousness, could not be visually observed |
| Comparative example 4 | $Fe_{1.06}(pz)[Ni_{0.98}Pd_{0.02}(CN)_4]$ | 12 | Unobviousness, could not be visually observed |
| Comparative example 5 | $Fe_{0.98}(pz)[Ni_{0.84}Pt_{0.16}(CN)_4]$ | 13 | Unobviousness, could not be visually observed |

(pz = pyrazine)

(Detection of Diethyl Carbonate Gas)

For the gas detection sheet of Examples 6 to 15, color tone change caused by DEC gas was evaluated in the same way as Example 1, and as the result, it was confirmed that the gas detection sheets turned to be orange. For the gas detectors of Comparative examples 3 to 5, color tone change caused by DEC gas was evaluated in the same way as Example 1, and as the result, the color tone changes after 80 minutes were unobviousness and thus could not be visually observed.

(Detection of the Leaked Gas of the Lithium Ion Secondary Battery and Determination of the Gas Leaking Position)

For the gas detection sheets of Examples 6 to 15, detection of the leaked gas of the lithium ion secondary battery and determination of the gas leaking position were evaluated in the same way as Example 1, and the color tone change of the gas detection sheet was evaluated in the same way as Example 1. As the result, it was confirmed that the color of the vicinity of the positive electrode terminal in the lithium ion secondary battery formed with pinhole changed to be orange. For the gas detection sheets of Comparative Examples 3 to 5, detection of the leaked gas of the lithium ion secondary battery and determination of the gas leaking position were evaluated in the same way as Example 1, and the color tone change of the gas detection sheet was evaluated in the same way as Example 1. As the result, it was confirmed that the color tone changes after 80 minutes were unobviousness and thus could not be visually observed.

Example 16

(Manufacturing of the Gas Detection Sheet)

A gas detection sheet prepared in the same way as in Example 1 was heated under 70° C. for one hour and thus a gas detection sheet was manufactured in which the porous coordination polymer was turned to be orange under a high-spin state.

(Detection of the Leaked Gas of the Electric Double Layer Capacitor and Determination of the Gas Leaking Position)

Two electric double layer capacitors containing acetonitrile in the electrolyte were prepared. Among these capacitors, a pinhole was punched artificially at a place near the positive electrode terminal of the double layer capacitor using needle to simulate the condition when a pinhole was existed on the case. The capacitors were wrapped using the gas detection sheet of Example 16 respectively and then put into the Tedlar bags and sealed to be placed for 3 minutes. The color tone change of the gas detection sheet of the electric double layer capacitor formed with pinhole was evaluated and it was confirmed the color changed to be reddish purple. 10 μL of gas in the Tedlar bag was fetched using a gas-tight syringe and the components were analyzed using a gas chromatograph, and as the result, about 20 ppm of acetonitrile was detected. On the other hand, the gas in the Tedlar bags with the electric double layer capacitor of which the gas detection sheet did not change was fetched and the content was analyzed. As the result, no gas content from electrolyte solution could be detected.

Example 17

(Manufacturing of the Gas Detection Sheet)

A polyvinylidene chloride transparent film was attached to the gas detection sheet prepared in the same way as in Example 1 with an adhesive to cover the whole of one surface as a protective film to prepare a gas detection sheet.

(Detection of the Leaked Gas of the Lithium Ion Secondary Battery and Determination of the Gas Leaking Position)

A lithium ion secondary battery was prepared. A pinhole was punched artificially at a place near the positive electrode terminal of the lithium ion secondary battery using needle to simulate the condition when a pinhole was existed on the case. The batteries were wrapped using the gas detection sheet of Example 17 with the protective film being outside and then put into a Tedlar bag of 5 L. The bag was filled with nitrogen containing ethanol gas to have a concentration of 10 ppm and sealed to be placed for 63 minutes. The color tone changes of the gas detection sheets were evaluated. As the result, it could be confirmed that the color of only the vicinity of the positive electrode terminal in the gas detection sheet of Example 17 changed to be orange while the whole changed to be orange in the case using a gas detection sheet without forming a protective film.

It could be known from the results above that, the gas detection sheets of the examples were excellent in visibility and the gas leaking position could be determined. Further, gas could be detected easily with excellent sensitivity by using the electrochemical element provided with a gas detection sheet of the examples.

DESCRIPTION OF REFERENCE NUMERALS

1 . . . Porous coordination polymer
2 . . . Ferrous ion
3 . . . Tetracyanonickelate ion
4 . . . Pyrazine
5 . . . Gas detection sheet
6 . . . Porous coordination polymer
7 . . . Supporter
8 . . . Protective film

What is claimed is:

1. A colorimetric gas detection sheet, comprising a porous coordination polymer supported on a porous supporter,
wherein the polymer is represented by the following formula (1), $$Fe_x(pz)[Ni_{1-y}M_y(CN)_4] \qquad (1)$$

pz=pyrazine 0.95≤x<1.05, M=Pd or Pt, 0≤y<0.15,
wherein the air permeability of the gas detection sheet is 0.8 seconds/300 mL or more and 60 seconds/300 mL or less;
and, wherein the detection sheet changes color due to the presence of volatile organic compounds.

2. The gas detection sheet according to claim 1, wherein, a surface of the gas detection sheet is covered by a protective layer.

* * * * *